(12) United States Patent
Maurice

(10) Patent No.: US 7,393,350 B2
(45) Date of Patent: Jul. 1, 2008

(54) CRYO-SURGICAL APPARATUS AND METHODS

(75) Inventor: George T. Maurice, North Falmouth, MA (US)

(73) Assignee: ERBE Elektromedizin GmbH, Tuebingen (DE)

( * ) Notice: Subject to any disclaimer, the term of this patent is extended or adjusted under 35 U.S.C. 154(b) by 283 days.

(21) Appl. No.: 10/945,616

(22) Filed: Sep. 20, 2004

(65) Prior Publication Data

US 2005/0038422 A1 Feb. 17, 2005

Related U.S. Application Data

(63) Continuation-in-part of application No. 10/213,568, filed on Aug. 6, 2002, now Pat. No. 6,858,025.

(51) Int. Cl.
*A61B 18/02* (2006.01)
*A61B 18/18* (2006.01)

(52) U.S. Cl. .......................... 606/21; 606/23

(58) Field of Classification Search ............ 606/20–26, 606/41, 49, 50; 128/898
See application file for complete search history.

(56) References Cited

U.S. PATENT DOCUMENTS

| | | | |
|---|---|---|---|
| 4,015,606 A | 4/1977 | Mitchiner et al. |
| 4,946,460 A | 8/1990 | Merry et al. |
| 5,281,213 A | 1/1994 | Milder et al. |
| 5,452,582 A | 9/1995 | Longsworth |
| 5,658,278 A | 8/1997 | Imran et al. |
| 5,800,487 A | 9/1998 | Mikus et al. |
| 5,814,040 A | 9/1998 | Nelson et al. |
| 5,899,897 A | 5/1999 | Rabin et al. |
| 5,906,612 A | 5/1999 | Chinn |
| 6,017,361 A | 1/2000 | Mikus et al. |
| 6,074,412 A | 6/2000 | Mikus et al. |
| 6,190,378 B1 | 2/2001 | Jarvinen |
| 6,305,378 B1 | 10/2001 | Lesh |
| 6,379,348 B1 | 4/2002 | Onik |

(Continued)

FOREIGN PATENT DOCUMENTS

EP 86107026.6 5/1986

(Continued)

OTHER PUBLICATIONS

Supplementary Partial European Search Report, European Pat. App. 03766842.3, 6 pages (May 9, 2006).

(Continued)

*Primary Examiner*—Roy D Gibson
(74) *Attorney, Agent, or Firm*—Klarquist Sparkman, LLP

(57) ABSTRACT

Cryosurgical apparatus includes an elongate cryoprobe having an electrically conductive first portion and multiple cooling elements. A removable sheath having an electrically conductive second portion is received on the cryoprobe with its electrically conductive second portion spaced from the electrically conductive first portion of the cryoprobe. Electrical insulation is interposed between the first portion and the second portion. In operation, cooling elements in the cryoprobe cool the tissue around a portion of the cryoprobe while electromagnetic energy traveling between the first portion and the second portion heats tissue adjacent to the cooled tissue. The cooling alters the path of the electromagnetic energy by changing the electrical conductivity of the tissue in the region of the cryoprobe.

19 Claims, 12 Drawing Sheets
(3 of 12 Drawing Sheet(s) Filed in Color)

U.S. PATENT DOCUMENTS

| | | | |
|---|---|---|---|
| 6,540,740 B2 * | 4/2003 | Lehmann et al. | 606/22 |
| 6,648,880 B2 | 11/2003 | Chauvet et al. | |
| 7,097,641 B1 * | 8/2006 | Arless et al. | 606/20 |
| 2002/0040220 A1 | 4/2002 | Zvuloni et al. | |
| 2004/0082943 A1 | 4/2004 | Littrup et al. | |

FOREIGN PATENT DOCUMENTS

| | | |
|---|---|---|
| EP | 0395307 A2 | 10/1990 |
| EP | 0608927 | 8/1994 |
| GB | 2094636 | 9/1982 |
| RU | 1827193 | 7/1993 |
| SU | 1532868 | 12/1989 |

OTHER PUBLICATIONS

International Search Report and Written Opinion, PCT App. PCT/US05/33708, 6 pages (Aug. 22, 2006).

Supplementary Partial European Search Report, European Pat. App. 03766842.3, 5pp. (Feb. 23, 2006).

Klein, Rainer, "Analysis of the Glue Effect Between Active Electrode and Coagulate During RF Surgery," (1986).

Onik and Cohen, "Transrectal Ultrasound-Guided Percutaneous Radial Cryosurgical Ablation of the Prostate," *Cancer* 72:1291-1299 (1993).

Rubinsky, Boris, "Cryosurgery," *Annu. Rev. Biomed. Eng.* 2:157-187 (2000).

* cited by examiner

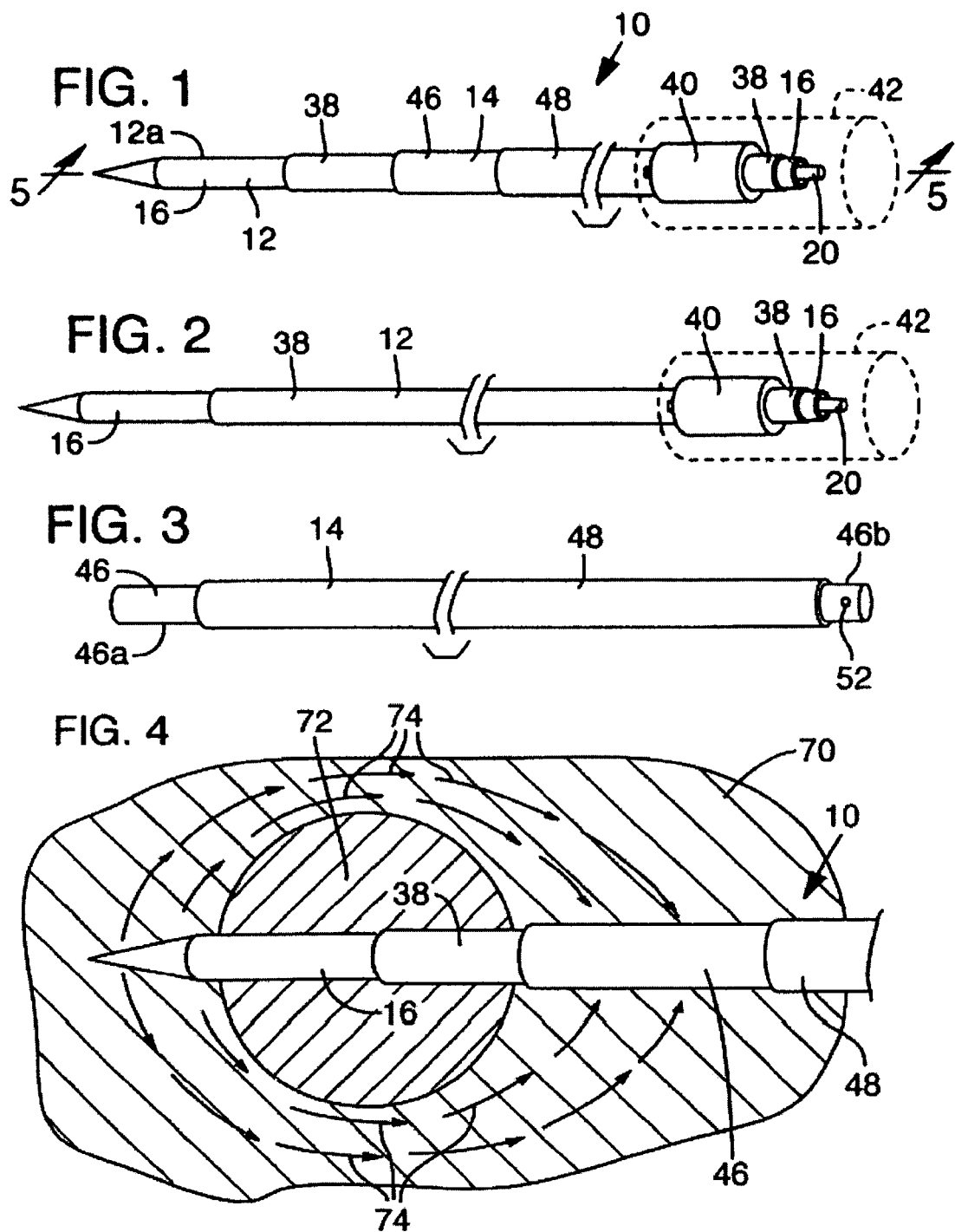

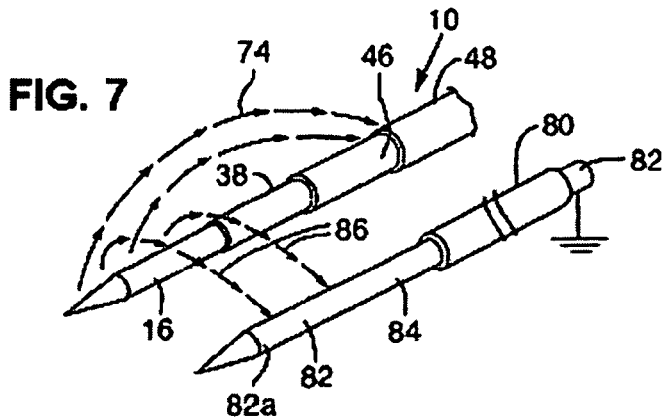
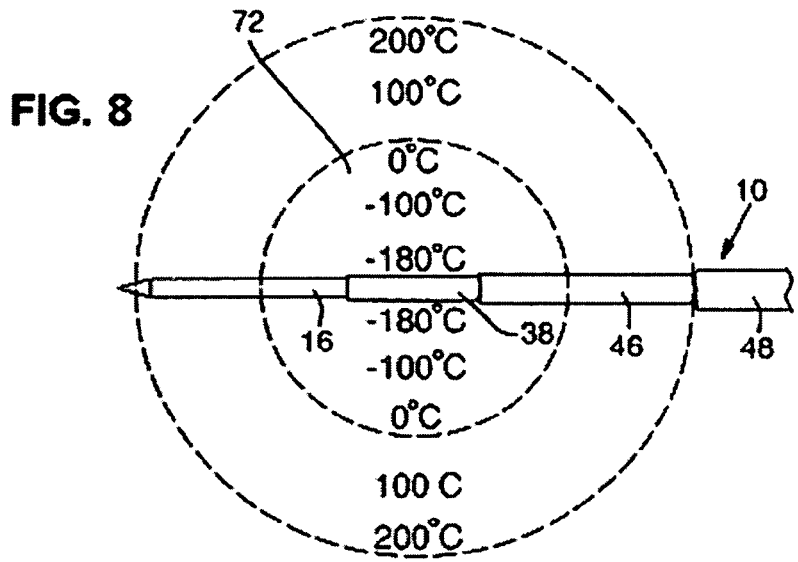
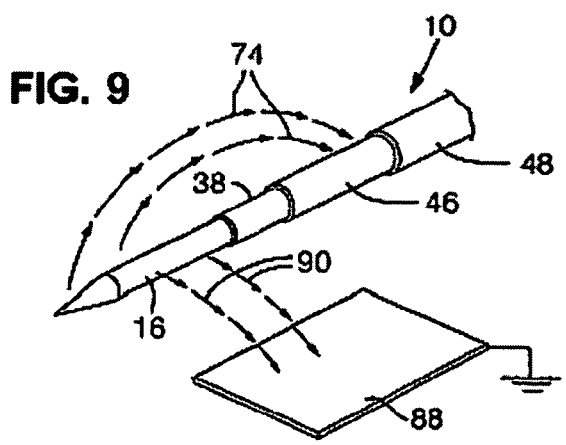

Our Ref. No.: 6661-67422-01
For: CRYO-SURGICAL APPARATUS AND METHODS
Express Mail Label No.: EV 339206088 US
Date of Deposit: September 20, 2004
Inventor(s): George T. Maurice
Sheet 9 of 12

$$y = 4 / [1 + e^{-0.3(x-7)}]$$

$R^2 = 0.894$

CRYO-SURGICAL APPARATUS AND METHODS

CROSS REFERENCE TO RELATED APPLICATION

This is a continuation-in-part application based on prior U.S. patent application Ser. No. 10/213,568, filed Aug. 6, 2002, now issued as U.S. Pat. No. 6,858,025, entitled Cryosurgical Apparatus and Method of Use. The prior application is incorporated herein by this reference.

FIELD

This application relates to cryoprobe apparatus and methods for use in cryosurgery and other applications, and more specifically to controlling size, shape, rate and/or other characteristics of coagulations formed in tissue.

BACKGROUND

Cryosurgery, or cryoablation, is one of the oldest of the local thermal ablation techniques. It was initially developed in the 19th century. It has been used for destroying and controlling tissue, such as tumors, deep within the body.

The use of cryosurgical probes for cryosurgery, or cryoablation, has been described in many clinical reports for the treatment of a variety of different benign and malignant tumors. In addition, the use of the cryosurgical probes for cryosurgery, or cryoablation, has been described in laparoscopic and percutaneous clinical reports.

A summary of the general history of cryosurgery and the mechanism involved therein is well set out in an article entitled "Cryosurgery," by Boris Rubinsky published in the *Annual Reviews in Biomedical Engineering*, 2:157-187 (2000), which is incorporated herein by reference.

Cryosurgery, or cryoablation, is a method of in situ freezing of tissues in which subfreezing temperatures are delivered through penetrating, or surface, cryoprobes in which a cryogen, or coolant agent or material, is circulated. The cryosurgical probe quickly freezes tissue adjacent the cryoprobe in order to cause cryonecrosis or tissue death. Irreversible tissue destruction generally occurs at temperatures below −20° C. Cell death is caused by direct freezing, cell membrane rupture, cell dehydration, denaturation of cellular proteins, and ischemic hypoxia. The necrotic tissue then is absorbed or expelled by the body. Multiple applications of freezing and thawing may be applied before the cryoprobes are removed.

This method of cryosurgery has a number of fundamental drawbacks. Presently, cryosurgery, or cryoablation, is primarily an open surgical technique. Depending on the tumor size, one to eight cryoprobes, ranging in diameter from 1.5-8 millimeters in size, are placed in the target tissue. A cryogenic material, typically liquid nitrogen or argon gas, is circulated through the cryoprobes for several minutes in order to achieve temperatures below −120° C. After a second freeze, the cryoprobes are heated, typically by circulating warming fluid or helium gas, and removed and the tracts are packed for hemostasis. Bleeding is often a common complication reported after the cryoablative or cryosurgical procedure. Additional complications include fever, renal failure, sepsis, disseminated intravascular coagulation, and leukocytosis. Other limiting factors include large cryoprobe sizes, damage to the tissue directly adjacent to the cryozone, and the size and the shape of the coagulations formed in the tissue.

For example, the use of cryosurgical probes in cryosurgery or cryoablation of the prostate is described in Onik and Cohen, "Transrectal Ultrasound-Guided Percutaneous Radial Cryosurgical Ablation of the Prostate," *Cancer* 72:1291 (1993), which details the cryosurgical or cryoablative procedure. The cryocoolers or cryoprobes are placed into the prostate gland through cannulas that were previously placed using ultrasound guidance. The irregular shape of the enlarged prostate gland requires a specific coagulation shape in order to treat the tissue completely. In order to prevent neighboring tissues or structures from being damaged, the urethra, external sphincter, and the bladder neck sphincter are protected from freezing by a continuous infusion of warm saline through a catheter placed in the urethra. Additionally, cryosurgery or cryoablation of hepatic metastasis poses a different challenge. Unlike primary hepatic tumors, for example hepatocellular carcinoma, the shapes of hepatic metastasis are irregular and typically are in poor locations whereby adjacent tissue or structure damage is a major concern.

The aforementioned difficulties in treating a variety of different benign or malignant tissues and the complications associated with current cryosurgical probes and cryoablative procedures has brought about the need for improved cryosurgical devices and methods.

SUMMARY

Disclosed are cryosurgical apparatus and methods of use capable of providing control over the configuration of the coagulation formed in tissue.

In one embodiment, an elongate cryoprobe has a cooling portion and an electrically conductive first portion in the region of the cooling portion, an energy conducting element is positioned adjacent the cryoprobe and has an electrically conductive second portion in a region spaced from the first portion on the cryoprobe, and a source of electromagnetic energy is operatively connected to one of the first and second portions operable to produce heating of tissue in the region of the coagulation to control configuration of the coagulation.

In an embodiment, the apparatus and method are such that electromagnetic energy is transmitted through the tissue surrounding a cooled or frozen area formed by the cooling portion of the cryoprobe with such energy heating the adjacent and surrounding tissue to expand or otherwise assist in controlling the configuration of the overall coagulation.

In some embodiments, the apparatus and/or method is capable of either protecting adjacent tissue or structure from thermal damage through selective heating of surrounding tissue, or may induce additional thermal damage to surrounding tissue by means of heat producing energy transmission.

In some embodiments of the invention, apparatus and/or method is provided for controlling the total amount of energy imposed in the adjacent tissue from both the thermal energy produced by the freezing mechanism and the electromagnetic power source energy, thus impacting the total amount of tissue necrosis.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 is a perspective view of a portion of apparatus according to one embodiment of the invention with an elongate centrally positioned cryoprobe surrounded by a sheath;

FIG. 2 is a view of the cryoprobe similar to FIG. 1 with the sheath removed;

FIG. 3 is a perspective view of the sheath removed from the cryoprobe;

FIG. 4 is an enlarged perspective view of the distal end portion of the cryoprobe apparatus inserted in tissue and operating to form a selectively configured coagulation;

FIG. 7 is a distal end perspective view of another embodiment of the invention;

FIG. 8 is an enlarged perspective view of the distal end portion of the cryoprobe apparatus that depicts an example of an operational thermal range;

FIG. 9 is a distal end perspective view of another embodiment of the invention;

DETAILED DESCRIPTION

Figure 5:
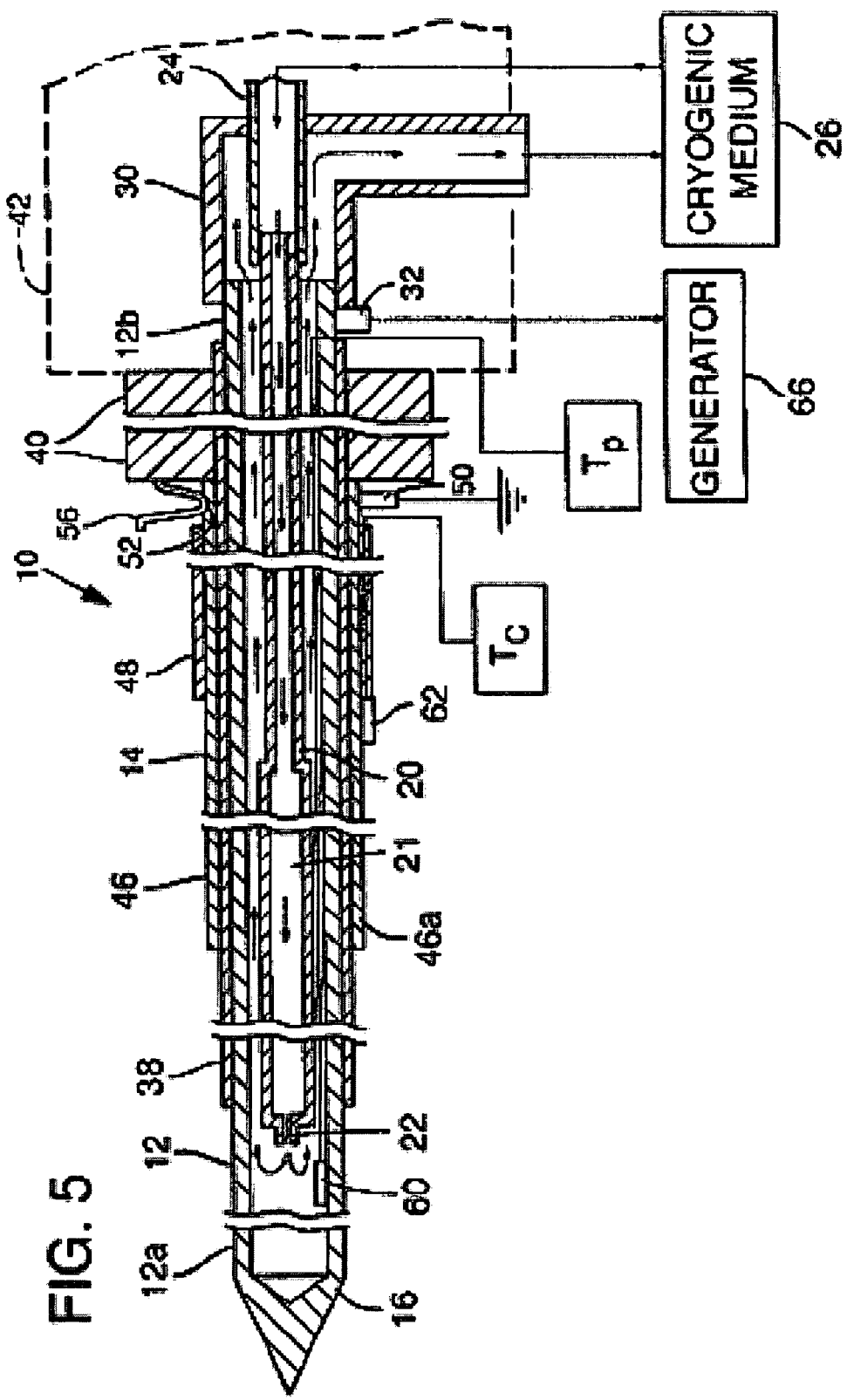
FIG. 5 is an enlarged cross-sectional view taken generally along the line 5-5 in FIG. 1, together with temperature displays, a return connector, a generator and a cryogenic medium supply.

The following terms are abbreviated in this disclosure as shown in parentheses: centimeters (cm), kilograms (kg), milligrams (mg), millimeters (mm), ohms ($\Omega$), pounds per square inch (psi), and radio frequency (RF).

The singular forms "a," "an," and "the" refer to one or more than one, unless the context clearly dictates otherwise. For example, the term "comprising a cryoprobe" includes a single cryoprobe or plural cryoprobes and is considered equivalent to the phrase "comprising at least one cryoprobe."

The term "or" refers to a single element of stated alternative elements or a combination of two or more elements. For example, the phrase "radiofrequency or microwave energy" refers to radiofrequency energy, microwave energy, or both radiofrequency and microwave energies.

The term "comprises" means "includes." Thus, "comprising A and B" means "including A and B," without excluding additional elements.

The term "proximal" refers to a portion of an instrument closer to an operator, while "distal" refers to a portion of the instrument farther away from the operator.

The term "subject" refers to both human and animal subjects. In certain embodiments, the subject is a human or other mammal.

The term "coagulation" refers to an area of tissue characterized by coagulation necrosis, such as coagulation necrosis resulting from cryoablation and/or electromagnetic ablation. In some uses, coagulations contain solid ice formations, and thus are sometimes familiarly referred to as "iceballs."

Referring to the drawings, and more specifically to FIGS. 1-3 and 5, at 10 is indicated generally an apparatus according to an embodiment of the invention. The apparatus includes an elongate cryoprobe 12 and a surrounding coaxially disposed sheath, or cannula, 14. The cryoprobe has a distal end 12a, and a proximal end 12b nearest the operator.

The cryoprobe includes an elongate hollow needle member 16 which is closed and pointed at its distal end and is open at its proximal end. An elongate coaxially disposed inner tube 20 is mounted within member 16. As seen in FIG. 5, tube 20, comprising a Giaque-Hampson heat exchanger 21 and a Joule-Thomson nozzle 22, ends toward the closed distal end of member 16 and extends outwardly from the proximal end of member 16. Tube 20 provides a cryogenic medium supply channel through which coolant, or refrigerant material, may be supplied to cryoprobe 12. A space provided between the outside of tube 20 and the inner walls of member 16 provides a return path for cryogenic medium to exit through the proximal end of member 16.

As best seen in FIG. 5, a tubing connector, such as that indicated generally at 24, may be operatively connected to the proximal end of tube 20 through which the cryogenic medium may be supplied from a cryogenic medium supply indicated generally at 26. A return connector 30 operatively connected to the proximal end of member 16 provides a return path for the cryogenic medium to return to the cryogenic medium supply 26 or to another region to which to it is desired to direct spent coolant fluid.

As indicated by the arrows in FIG. 5, cryogenic medium from cryogenic supply 26 is directed through tube 20, comprising a Giaque-Hampson heat exchanger 21 and a Joule-Thomson nozzle 22, toward the distal end of cryoprobe 12, exiting the Joule-Thomson nozzle 22 toward the distal end portion of member 16 which serves as an expansion chamber and cools toward the distal end 12a of the cryoprobe. Fluid then returns along the channel provided between tube 20 and the member 16 to exit the apparatus through return connector 30.

The member 16 is constructed of a thermally conductive material such that the distal end portion of member 16 serves as what may be considered a freezing tip, or cooling portion, which upon activation may freeze or cool tissue in which it is inserted.

Further, member 16 may be constructed of an electrically conductive material, such as surgical steel, and has an electrical connector 32 coupled to its proximal end, as illustrated in FIG. 5. This allows it to be operatively connected to electrical or electromagnetic equipment, as will be described further below, and to conduct electrical or electromagnetic energy between its proximal end and its distal end.

Although member 16 is described herein as being constructed generally of electrically conductive material throughout, such that energy may be conducted between its proximal end and its distal end, it should be recognized that portions of member 16 may be made of non-electrically conductive material and that only a portion adjacent the cooling portion of the cryoprobe, would have an electrically conductive exposed portion. In such case, appropriate conductors would extend between the electrically conductive portion on the member and the electrical connector 32 such that electrical energy could be transmitted therebetween.

A layer of electrical insulating material 38 covers the major portion of member 16 between its proximal and distal ends. As best seen in FIG. 5, the proximal end 12b of member 16 may be left somewhat exposed for the application of connector 32, and the distal end portion of member 16 remains exposed. The electrical insulating material may be a non-conducting rubber, plastic, or other polymer capable of insulating the tissue adjacent the insulating material. In some embodiments, the electrical insulating material is selected to be thermally transmissive, while still being capable of blocking the flow of electrical energy. The electrical insulating material also may be selected to be manufacturable to exacting tolerances. One example of a suitable electrical insulating material is polyester. Some embodiments of the disclosed cryosurgical device use polyester tubing, such as part #06100CST from Advanced Polymers (Salem, N.H.). By way of theory, the thermal transmissivity of the electrical insulation may be improved by decreasing its thickness. For example, part #06100CST has a wall thickness of only 0.0025 cm +/−0.0005 cm.

A mounting sleeve 40 is secured to a proximal end portion of cryoprobe 12 and serves to have a holder, such as that indicated generally dashed outline at 42, providing a hand hold through which an operator may grasp and manipulate the apparatus during use. Since the holder 42 may take many different forms, it is shown here only in a generalized form.

Referring to FIGS. 3 and 5, sheath 14 comprises an elongate cannula 46 having a distal end 46a and proximal end 46b. The cannula has a central opening, or lumen, sized to slidably receive member 16 and its associated electrical insulating material 38 therethrough. Cannula 46 has a layer of electrically insulating material 48 covering a major portion thereof. The electrical insulating material covering the cannula may be similar to that used on member 16. The distal and proximal ends of cannula 46 are not covered by insulating material, but are left exposed as best illustrated in FIGS. 3 and 5.

Cannula 46 may be made of an electrically conductive material and has an electrical connector 50 attached to its proximal end, such that electrical energy may be transmitted between the distal end 46a and proximal end 46b of cannula 46. In an alternate construction, the cannula may be made of a non-electrically conductive material with an electrically conductive portion provided at its distal end 46a and appropriate electrical conductors connecting such electrically conducting portion at its distal end to a connector such as that indicated at 50 whereby electrical energy may be transmitted between such points.

A detent 52 is formed in the proximal end portion 46b of cannula 46. A yieldable interlock mechanism 56 secured to mounting sleeve 40 is positioned to releasably engage detent 52 to hold sheath 14 on cryoprobe 12 as illustrated in FIG. 5. The interlock mechanism is spring biased into the holding position illustrated in FIG. 5. The mechanism is easily released by manually urging the interlock mechanism from detent 52 allowing the sheath 14 to be slid off of cryoprobe 12.

The apparatus, as illustrated in FIGS. 1 and 5, has sheath 14 mounted coaxially on cryoprobe 12 and held in place by interlock mechanism 56. In this position electrical insulating material 48 covers the major portion of the length of cannula 46, leaving its distal end portion 46a exposed. Electrical insulating material 38 surrounding a major portion of the length of needle member 16 electrically insulates cannula 46 from member 16. As best seen in FIGS. 1 and 5, electrical insulation material 38 extends longitudinally outwardly from the distal end portion 46a of cannula 46. The distal end of member 16 extends longitudinally outwardly from insulating material 38 and from cannula 46, such that the distal end portion of member 16 is both electrically and thermally exposed.

Although cryoprobe 12 and sheath 14 are shown as having a circular cross-section it should be understood that other cross-sections also are acceptable. These could include oval, rectangular, triangular or others. Similarly, the illustrated embodiments of the cryoprobe and sheath are straight, but curved embodiments also are acceptable. Curved embodiments can be used, for example, to access tissue that would be difficult to access with straight embodiments.

Referring to FIG. 5, a temperature sensing thermocouple 60 mounted within cryoprobe 12 is operable to determine the temperature at the distal end portion of the cryoprobe and transmit such information to a registering instrument indicated at $T_P$. Similarly, a thermocouple 62 associated with cannula 46 is operable to transmit information regarding temperature in the distal region of the cannula to a temperature registering device indicated at $T_C$.

Referring still to FIG. 5, the needle member 16 and cannula 46 are adapted for connection to apparatus for providing heat energy to tissue in a region adjacent the cryoprobe. In the illustrated embodiment, needle member 16 is connected through electrical connector 32 to an electromagnetic energy generator 66, which in the illustrated embodiment may be a radio frequency (RF) generator, a microwave generator, or other appropriate variable frequency electromagnetic energy generator. Cannula 46 is shown as operatively connected through its electrical connector 50 to electrical ground. In alternate embodiments cannula 46 could be connected to the energy generator and cryoprobe 12 connected to ground.

Commercially available electromagnetic energy generators may be used in the system to produce the desired RF energy, microwave energy, or other appropriate variable frequency electromagnetic energy. Those skilled in the field will be well versed in the types of electromagnetic energy generators which may be appropriate for producing the types and levels of electromagnetic energy required to provide the desired results for controlling the configuration of the coagulation produced. The electromagnetic energy supplied to the apparatus can be controlled in either a modulated or pulsed fashion.

Similarly, the cryogenic material supply used in the system may be any commercially available cryogenic material supply appropriate for such operation, as are well known to those skilled in the field.

Explaining operation of the apparatus thus far disclosed, and referring initially to FIG. 4, the distal end of apparatus 10 is inserted into tissue 70 of a subject to be treated. The sharpened distal end of needle member 16 facilitates insertion. After the cryoprobe has been inserted to a desired target location within the tissue, a cryogenic medium from cryogenic medium supply 26 is supplied to member 16, such that tissue in the region surrounding and adjacent the cooling portion of the cryoprobe is frozen as indicated at 72.

After the coagulation begins to form, electromagnetic energy from generator 66, such as radio frequency or microwave energy or other appropriate variable frequency electromagnetic energy, is supplied to conductive needle element 16 while electrically conductive cannula 46 is connected to ground. Electromagnetic energy transmitted to the distal end of needle member 16 flows from member 16, through tissue 70 surrounding frozen tissue 72 to grounded cannula 46, as illustrated generally by arrows 74 in FIG. 4. The transmission of electromagnetic energy through the tissue adjacent and surrounding the coagulation serves to heat such surrounding tissue and control the configuration of the coagulation. The extent of control over the configuration of the coagulation is related to the level and timing of the energy transmitted between the needle member 16 and the cannula 46 through tissue 70 surrounding frozen tissue 72.

The combination of cryoablation and electromagnetic ablation is capable of causing a greater amount of tissue death than either cryoablation alone or electromagnetic ablation alone. By way of theory and not to limit the scope of the disclosure, the synergies achieved by combining these two techniques may result, in part, from their effects on the electrical conductivity of the tissue being treated. The electrical conductivity of tissue is highly dependent on temperature. Freezing generally decreases tissue's electrical conductivity, while heating generally increases tissue's electrical conductivity. Thus, when cryoablation and electromagnetic ablation are performed simultaneously, tissue closer to the cooling source will be colder and have lower electrical conductivity than tissue further from the cooling source. Under these conditions, the current tends to travel outward from the cooling source to find tissue of higher electrical conductivity.

When viewed in any plane, the path of least resistance is generally elliptical in shape if formed about two electrodes spaced along an axis. The arrows 74 in FIG. 4 illustrate the path favored by the electromagnetic energy around the cooling source, which is located in the needle member 16. Since the path of least resistance expands outward as the cooling activity increases, ablation caused by the electromagnetic energy can supplement any ablation caused by the cooling activity. In Examples 3 and 4 (below), the effects of cryoablation in combination with electromagnetic ablation were observed at greater distances from the cryoprobe (as shown by the larger elliptical pattern in FIG. 4) in comparison to cryoablation alone or electromagnetic ablation alone.

The path of the electromagnetic energy depends on the relative electrical conductivity of the tissue at varying distances from the cryoprobe. In some implementations, the cooling activity of the cryoprobe will form a substantial mass of frozen tissue characterized by very low electrical conductivity. In other implementations, the cooling activity of the cryoprobe will freeze a very small amount of tissue and/or simply maintain the tissue closest to the cryoprobe at its normal electrical conductivity or even above its normal electrical conductivity, while the tissue further from the cryoprobe experiences substantially increased electrical conductivity due to heating from the electromagnetic energy.

The formation of a substantial mass of frozen tissue is more likely to occur at low current densities. At high current densities, it is more likely that the cryoablation will maintain the tissue near the cryoprobe at its normal electrical conductivity or above its normal electrical conductivity. As long as the electrical conductivity of the tissue closest to the cryoprobe is lower than the electrical conductivity of the tissue further from the cryoprobe, thus maintaining a conductivity differential, the path of the electromagnetic energy will be directed outward from the cryoprobe. If the cooling activity is gradually increased, the path of the electromagnetic energy will expand outward from the cryoprobe and is capable of destroying tissue as it expands. Thus, in some implementations, a mass of tissue in the treatment area will be destroyed primarily by the electromagnetic energy and the cooling activity will merely serve to grow the ablation zone by gradually expanding the path of the electromagnetic energy.

Figure 6A:
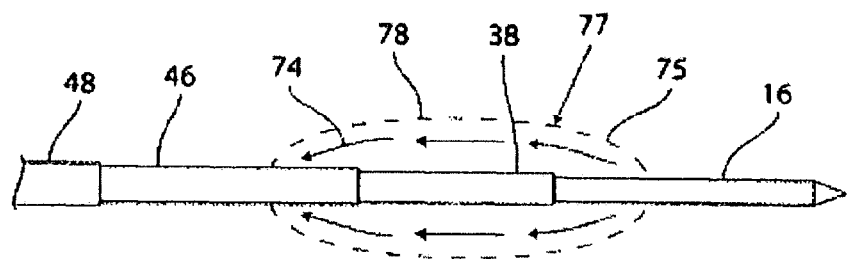
FIGS. 6A-6C are enlarged perspective views of the distal end portion of the cryoprobe apparatus showing how the cooling activity of the cryoprobe apparatus can be used to modify the path of the electromagnetic energy and thereby form an enlarged coagulation.
Figure 6B:
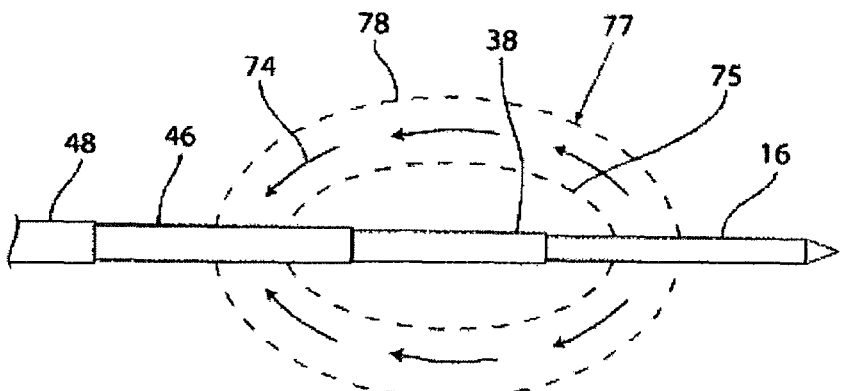
Figure 6C:
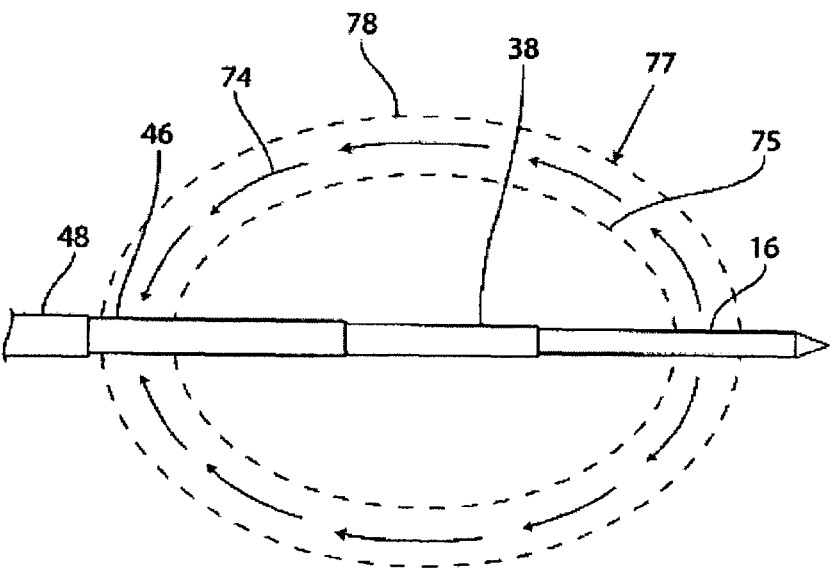

FIGS. 6A-C illustrate the use of cooling activity to expand the path of the electromagnetic energy. As in FIG. 4, arrows 74 indicate the path favored by the electromagnetic energy. In this implementation, heat from the electromagnetic energy causes tissue death in an electromagnetic ablation zone 75. FIG. 6A shows the cryosurgical apparatus operating in tissue before the tissue has been significantly cooled, such as immediately after insertion of the cryosurgical apparatus into a patient. The electromagnetic energy takes the shortest path between the needle member 16 and the cannula 46, which is a path intimately surrounding the cryosurgical apparatus. In FIG. 6B, the cooling activity of the cryosurgical apparatus has produced a cooling zone 76. The cooling zone 76 has a decreased electrical conductivity compared to tissue further from the cryosurgical apparatus. Thus, the path of the electromagnetic energy and the electromagnetic ablation zone 75 are extended away from the cryosurgical apparatus. The development of the cooling zone 76 can be timed so that the tissue in the cooling zone has already been killed by heating from the electromagnetic energy before it is cooled or frozen by the cryogenic activity. FIG. 6C shows further growth of the cooling zone 76, which pushes the path of the electromagnetic energy and the electromagnetic ablation zone 75 even further from the cryosurgical apparatus. The total ablation zone 77 has a short axis diameter along a line 78 perpendicular to the length of the cryosurgical apparatus. From FIG. 6A to FIG. 6C, it is evident that the total ablation zone 77 has been expanded by cooling the tissue adjacent to the cryosurgical apparatus. Depending on the intensity of the cooling activity, the tissue death in the total ablation zone 77 can be a result of electromagnetic ablation alone or a combination of electromagnetic ablation and cryoablation.

The combination of cryoablation and electromagnetic ablation has been shown to enable the stable application of greater amounts of current than electromagnetic ablation alone. In Examples 3 and 4, electromagnetic ablation was performed reliably at 0.7 amperes when it was applied in combination with cryoablation. In contrast, without cryoablation, currents above 0.4 amperes led to rapid, irreversible impedance rises. Under certain conditions, tissue coagulation is directly proportional to the amount of applied current. Thus, by way of theory and not to limit the scope of the disclosure, the increased current available with the combination of cryoablation and electromagnetic ablation may contribute to the increased tissue death. In some implementations, it may be advantageous to apply electromagnetic energy at currents greater than about 0.5 amperes, such as currents greater than about 0.6 amperes.

Cryoablation also may cause cellular changes that improve the efficiency of electromagnetic ablation. These cellular changes may include, for example, dehydration and protein denaturation. With less water to heat, more thermal energy may be absorbed by cellular proteins and other cellular components resulting in more efficient cellular destruction. Likewise, cells injured by cryoablation are likely to be more susceptible to injury via thermal heating.

As is know by those skilled in the art, the propagation of electromagnetic energy through tissue is frequency dependent. The operator will choose an appropriate frequency to produce the desired control of the configuration and size of the coagulation formed.

The cryogenic material preferably will be able to cool tissue to temperatures in a range of about 0° C. to −180° C. or lower.

The electromagnetic energy to which the tissue is exposed may be capable of causing tissue to be heated to temperatures from 10° C. to 200° C. or more.

Although cooling temperatures to −180° C. and heating temperatures to 200° C. have been noted, it should be recognized that the supply of the cryogenic medium to the cryoprobe may be controlled to produce appropriate freezing temperatures for tissue in the region of the cooling portion of the cryoprobe and the heating temperature for tissue may be controlled by the appropriate supply of electromagnetic energy from generator 66. The cooling temperatures used for freezing tissue and the heating temperatures used for heating tissue will be chosen by the operator as most appropriate for the procedure.

FIG. 8 illustrates an example of temperature ranges produced in tissue surrounding the apparatus during use. As shown, the temperature gradients in tissue may range from a low of about −180° C. contiguous to the cryogenic portion of the apparatus to a high of about 200° C. spaced a distance therefrom with a range of intermediate temperatures therebetween. The temperature gradients shown here are examples only.

The temperature used for freezing or cooling is measured by thermocouple 60 in needle member 16 and is registered on device $T_P$. Similarly, the heating temperature adjacent the apparatus may be judged from the temperature reading from thermocouple 62 on cannula 46 and noted on registering device $T_C$.

As an example only, the cryoprobe 12 generally may be any suitable length and diameter needed for selected procedures. In some embodiments, the cryoprobe may have a length of about 10 cm to 25 cm and a diameter of about 0.1 to 0.8 cm. The non-insulated distal end portion 12*a* of cryoprobe 12 would project about 2 cm from the outer end of insulating covering 38. Insulating covering 38 would project approximately 0.5 cm longitudinally outwardly from cannula 46 and exposed distal end portion 46*a* of cannula 46 could extend approximately 2 cm outwardly from its insulating covering 48. These, however, are exemplary dimensions only. The size of components and the portions exposed both for thermal conductivity and electrical conductivity may be altered for different embodiments and to provide selected cooling and heating capabilities.

FIG. 7 illustrates another embodiment in which a second electrically conductive element 80 is used. Electrically conductive element 80 includes an elongate electrically conductive member 82 having a sharpened distal end 82*a* for insertion into tissue and a covering of electrically non-conductive material 84 covering a major portion of the length of element 80, but leaving the distal end 82*a* exposed. Member 82 is connected to electrical ground as indicated.

In operation of the apparatus shown in FIG. 7, cryoprobe apparatus 10 is inserted into tissue to be treated as previously described and appropriately connected to the cryogenic medium supply 26, generator 66 and electrical ground. Element 80 is inserted into tissue adjacent and spaced laterally from cryoprobe 12, with the exposed portion of member 82 aligned as desired with the exposed cooling portion and electrically conductive portion of needle member 16.

When energy from generator 66 is transmitted to needle member 16, such energy will flow not only to grounded cannula member 46 as indicated by arrows 74, but also to grounded member 82, as indicated by arrows 86. With member 82, and possibly other similar electrically conductive elements placed adjacent but spaced laterally from the cryoprobe, the electromagnetic energy transmitted through the tissue will serve to further control the configuration of a coagulation generated by cryoprobe apparatus 10.

FIG. 9 illustrates another embodiment in which a second electrically conductive element 88, also referred to as a dispersive electrode, is used. Element 88 comprises an electrically conductive plate which is electrically grounded. The plate may be placed against the skin of a subject in which the cryoprobe apparatus is to be used.

In operation of the apparatus shown in FIG. 9, cryoprobe apparatus 10 is inserted into tissue to be treated and appropriately connected to the cryogenic medium supply 26, generator 66, and electrical ground. Element 88 is placed in contact with the skin of a subject to be treated in a region appropriately chosen by the operator. When energy from generator 66 is transmitted to needle member 16 such energy will flow not only to grounded cannula member 46 as indicated by arrows 74, but also to grounded member 88 as indicated by arrows 90. The electromagnetic energy transmitted between needle member 16 and member 88 will serve to further control the configuration of a coagulation generated by cryoprobe apparatus 10.

Figure 10:
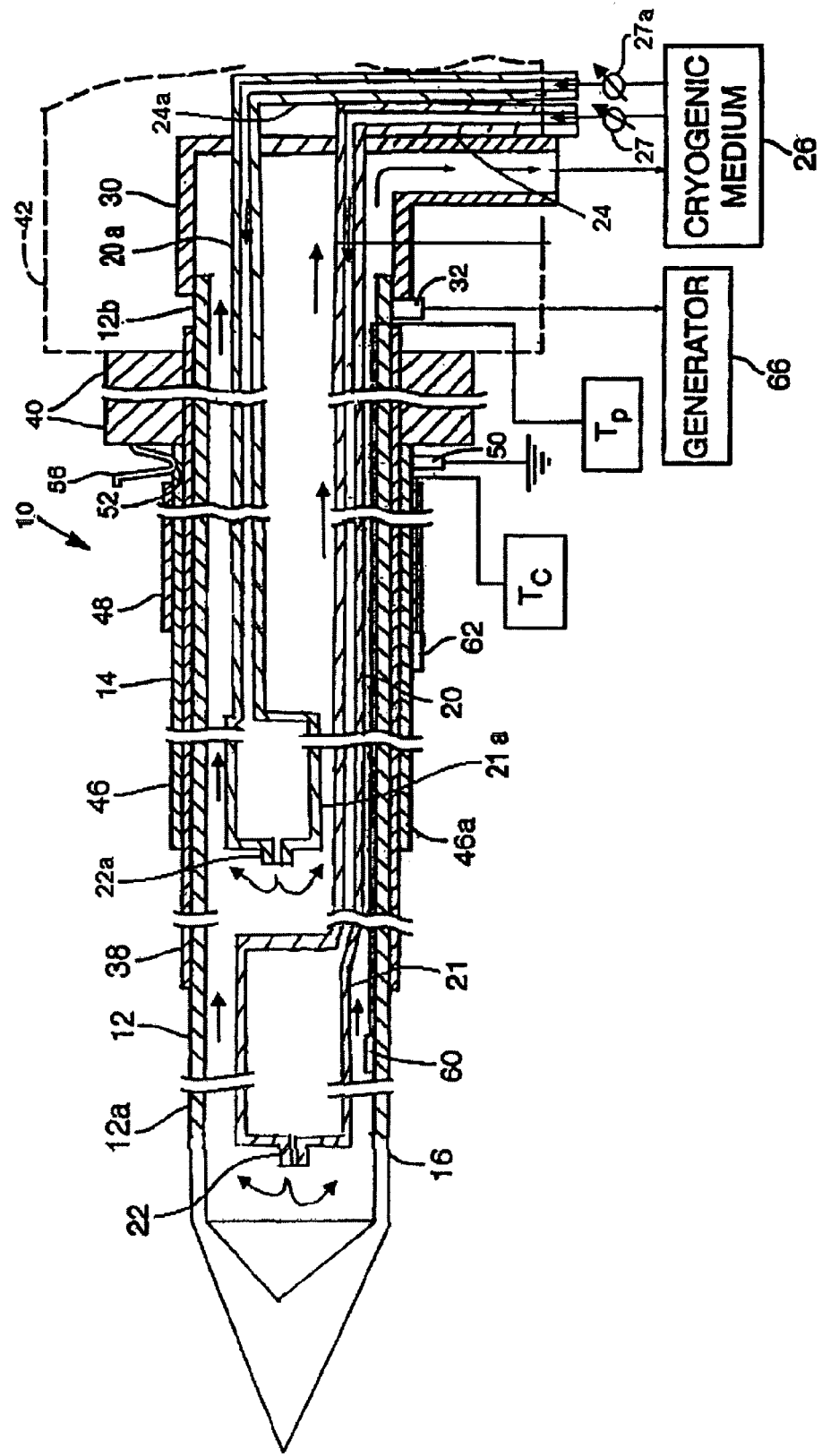
FIG. 10 is an enlarged cross-sectional schematic view of an embodiment of the cryosurgical apparatus having dual heat exchangers and variable supply valves, together with temperature displays, a return connector, a generator and a cryogenic medium supply.

FIG. 10 illustrates another embodiment of the disclosed cryosurgical apparatus. Many of the reference numerals used in FIG. 5 are repeated in FIG. 10 to indicate similar or identical elements. Similar to the embodiment illustrated in FIG. 5, the embodiment illustrated in FIG. 10 is capable of using electromagnetic energy in combination with cryogenic activity to perform tissue ablation. The embodiment illustrated in FIG. 10 has multiple cooling sources that are selectively controllable to improve the versatility and capacity of the apparatus. For example, the embodiment shown in FIG. 10 comprises a second tube 20*a* comprising a second heat exchanger 21*a* and a second nozzle 22*a*. The second heat exchanger 21*a* and the second nozzle 22*a* are positioned along the length of the cryoprobe 12 between the previously described heat exchanger 21 and the proximal end of the cryoprobe 12*b*. The second tube 20*a* is connected to a tubing connector 24*a*, through which the cryogenic medium may be supplied from the cryogenic medium supply 26. The embodiment shown in FIG. 10 also comprises variable control valves 27 and 27*a* to control the flow of cryogenic medium from the cryogenic medium supply 26 into tubing connectors 24 and 24*a*, respectively.

Multiple heat exchangers, as shown in FIG. 10, have several advantages over a single heat exchanger. First, multiple heat exchangers generally are capable of producing greater cooling than a single heat exchanger. While it may be possible to increase the cooling produced by a single heat exchanger, e.g. by increasing its size, doing so may result in an increase in coolant pressure. Due to structural limitations, heat exchangers, which in some embodiments include a serpentine tube and an expansion valve, are limited in their ability to handle high pressures. This is particularly true with regard to heat exchangers that are configured to fit in small spaces, such as the inside of a cryoprobe.

Figure 11:
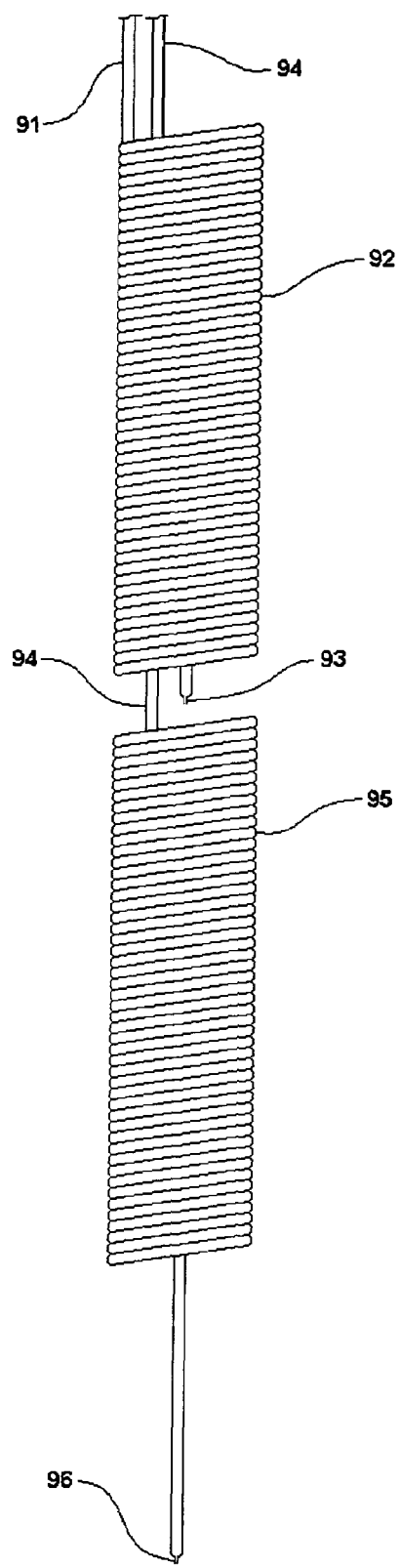
FIG. 11 is an enlarged schematic plan view of two heat exchangers configured for use with an embodiment of the cryosurgical apparatus.

Some embodiments of the cryosurgical apparatus comprise dual heat exchangers that are specially configured to fit within a long and narrow cryoprobe. FIG. 11 shows an example of one such configuration. A first heat exchanger comprises a first supply tube 91, a first serpentine tube portion 92 and a first nozzle 93. A second heat exchanger comprises a second supply tube 94, a second serpentine tube portion 95 and a second nozzle 96. The first serpentine tube portion 92 wraps around the second supply tube 94. This not only saves space, it also provides extra cooling for the second serpentine tube portion 95. The extra cooling of the second serpentine tube portion 95 allows the second nozzle 96 to provide enhanced cryogenic activity.

Multiple heat exchangers also can be used to improve the versatility of the cryosurgical apparatus. An operator using a cryoprobe with multiple heat exchangers positioned at different points along its length can selectively activate one or more of these heat exchangers to produce effects in the tissue adjacent these points and surrounding tissue, as desired. The operator also can activate the heat exchangers in different combinations to control the shape and size of the affected tissue mass. For added control, the positions of the heat exchangers can be adjustable along with their cooling rates and sequence of operation.

Incorporating variable supply valves to control the flow of coolant into each heat exchanger further improves the versatility of embodiments of the cryosurgical apparatus comprising multiple heat exchangers. Variable supply valves allow the operator to control the degree of cooling activity generated by each heat exchanger. The operator can, for example, adjust the variable supply valves to modify the cooling activity produced by the heat exchangers in response to real-time information about the coagulation, such as real-time information about the shape and size of the coagulation as it develops. Such information can be provided, for example, by ultrasound or other type of monitoring.

FIGS. 12A-D show several embodiments of the disclosed cryosurgical apparatus forming coagulations in tissue. Each embodiment comprises a cryoprobe with multiple heat exchangers positioned at different points along its length. Two heat exchangers are activated in each illustrated embodiment. The positioning of the heat exchangers, as well as how they are operated, affects the size and shape of the coagulations.

Figure 12A:
FIGS. 12A-12D are cross-sectional views of the distal end portions of embodiments of the cryosurgical apparatus comprising dual heat exchangers positioned at different points along the length of the cryoprobe to produce coagulations of different shapes and sizes.

To facilitate comparison, the two active heat exchangers in each of the illustrated embodiments are operated identically with the only difference being their positions along the cryoprobe. In FIG. 12A, a cryosurgical apparatus 100 comprises heat exchangers 102 and 104 positioned close together near its distal end. The cryosurgical apparatus 100 produces a coagulation 106 that is generally ellipsoidal in shape. This shape results from the close spacing of the heat exchangers and the commingling of their cooling activity.

Figure 12B:
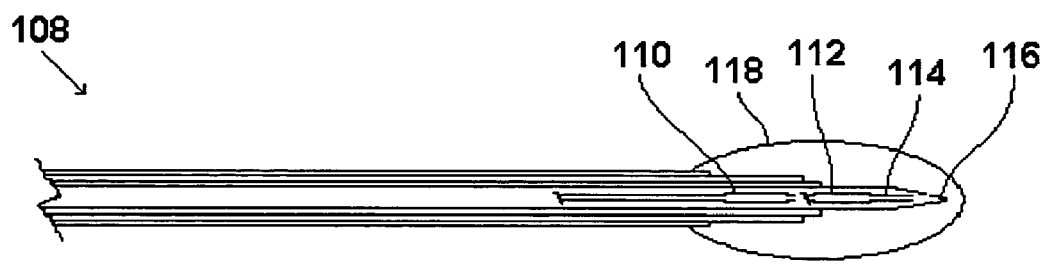

FIG. 12B shows a cryosurgical apparatus 108 comprising heat exchangers 110 and 112. Like the heat exchangers in FIG. 12A, the heat exchangers 110 and 112 are positioned close together near the distal end of the cryosurgical apparatus 108. The heat exchanger 112, however, is connected to an extended Joule Thomson nozzle 114 that is narrow enough to fit inside the distal tip 116 of the cryosurgical apparatus 108. The extended Joule Thomson nozzle 114 allows the cooling activity of the heat exchanger 112 to be moved closer to the distal tip 116. The resulting coagulation 118 is ellipsoidal and longer than the coagulation shown in FIG. 12A.

Figure 12C:
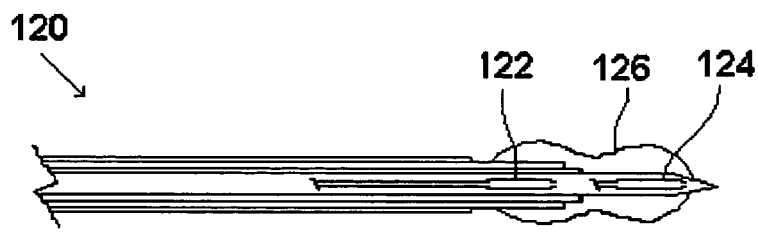

FIG. 12C shows a cryosurgical apparatus 120 comprising heat exchangers 122 and 124 positioned further apart than the heat exchangers in FIGS. 12A and 12B. Coagulation 126 formed by the cryosurgical apparatus 120 has an hourglass shape in section or an overall "dog bone" shape.

Figure 12D:
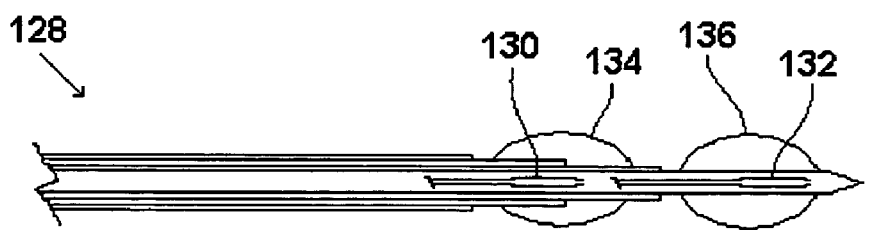

FIG. 12D shows a cryosurgical apparatus 128 comprising heat exchangers 130 and 132 positioned even further apart than the heat exchangers in FIG. 12C. With the heat exchangers 130 and 132 positioned this far apart, two separate, generally spherical coagulations 134 and 136 are formed, one around each of the heat exchangers 130 and 132.

Figure 13A:
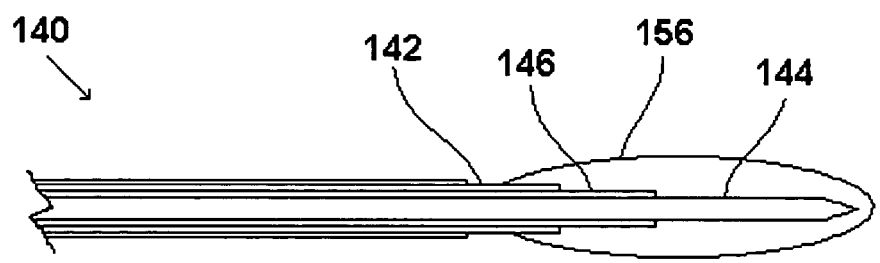
FIGS. 13A and 13B are enlarged cross-sectional views of the distal end portions of embodiments of the cryosurgical apparatus with different lengths of exposed insulation between the cannula and the cryoprobe.
Figure 13B:
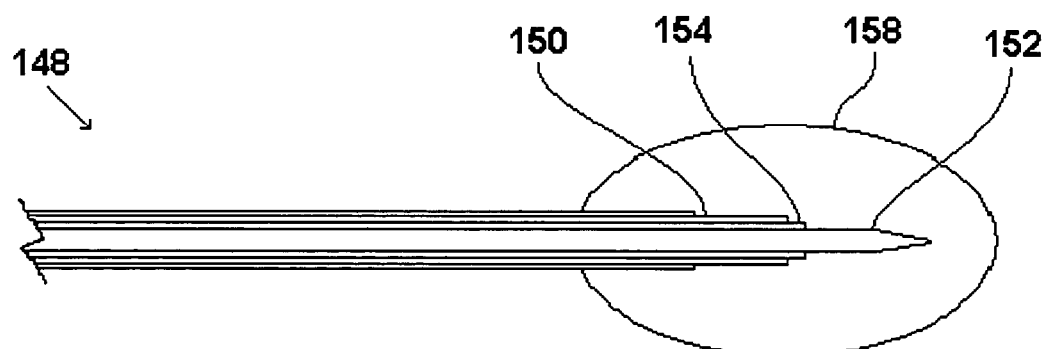

The size and shape of the coagulations formed by the disclosed cryosurgical apparatus also can be affected by the distance between the two electrodes. This distance can be, for example, the length of the exposed electrical insulation separating the electrically conductive cryoprobe from the electrically conductive cannula. FIGS. 13A and 13B show two embodiments of the disclosed cryosurgical apparatus with different amounts of separation between the two electrodes. In FIG. 13A, cryosurgical apparatus 140 comprises a cannula 142 and a cryoprobe 144 separated by insulation 146. In FIG. 13B, cryosurgical apparatus 148 comprises a cannula 150 and a cryoprobe 152 separated by insulation 154. In cryosurgical apparatus 140, there is a greater length of exposed insulation than in cryosurgical apparatus 148. This forces the electromagnetic energy traveling between the cryoprobe 144 and the cannula 142 to take a longer and narrower path. As a result, the coagulation 156 formed by cryosurgical apparatus 140 is longer and narrower than the coagulation 158 formed by cryosurgical apparatus 148.

As illustrated in FIGS. 12 and 13, coagulations of different sizes and shapes can be formed by modifying the positions of the heat exchangers and by modifying the amount of separation between the electrodes. The ability to form coagulations of different sizes and shapes can be beneficial for improving selectivity during ablation procedures, particularly when the tissue to be destroyed is not perfectly spherical.

Although the apparatus has been described in the configurations illustrated and as set out above, it should be recognized that other forms also could be used which would function as desired. For example, the cooling portion of the cryoprobe might be disposed intermediate the ends of the apparatus and the exposed conducting element could be disposed toward, or at, the distal end of the apparatus. It is, however, important that electrically insulating material be interposed between the two electrically conductive components (one of which receives electromagnetic energy from the generator and the other of which is connected to ground) such that tissue heating energy will flow through tissue extending about the cooled tissue around the cooling portion of the cryoprobe.

The method for producing appropriate cooling or freezing and control of the configuration of the coagulation may be further enhanced by modifying (increasing or decreasing) the electrical and thermal conductivity characteristics of tissue in the region of the cryoprobe, thus impacting the total amount of tissue necrosis. This may be accomplished by introducing various agents into the tissue, the agents being selected based on biocompatibility, thermal and electrical properties. Such agents are known by those skilled in the art.

The therapeutic effect of apparatus and method of operation thus far described also may be further enhanced by the injection of elements that have encapsulated agents therein which are released by heat. The injection of such materials into regions of tissue adjacent the cryoprobe apparatus permits heat generated from the electromagnetic energy generators to release agents from their encapsulated state to provide additional therapeutic effects.

EXAMPLES

The following examples are provided to illustrate certain particular embodiments of the disclosure. It should be understood that additional embodiments not limited to the particular features described are consistent with the following examples.

The ablations or coagulations formed in the following examples have a long axis parallel to the cryoprobe's length and a short axis perpendicular to the cryoprobe's length. The coagulation diameter, i.e., the diameter of the ablation, on the short axis was used as the primary outcome measure for the statistical analyses in Examples 3 and 4. Student's T-tests were used to determine statistical significance ($\alpha=0.05$; two-tailed test) using Origin 6.1 (Northampton, Mass.). Univariate and multivariate regressions were performed using Origin 6.1 and Excel 2002 to produce best-fit curves and $R^2$ computation for linear and higher order regression models. Three-dimensional contour plots of argon pressure, RF current, and coagulation dimensions were computed using DPlot 1.7.5 engineering software (Vicksburg, Miss.).

Diameters on the long axis were included in Example 3 in order to suggest the size of a tumor potentially treatable. The shape of ablations was ellipsoidal and completely contiguous unless otherwise stated.

Example 1

Constructing the Cryosurgical Apparatus

A RF ablation system including positive and negative electrodes was combined with a cryoablation device within an 18-gauge needle shaft (The Cunningham Group, Cummings, Ga.). The RF system consisted of an active 2.5 cm tip with a 2.5 cm return pole located 3 mm proximally from the active tip. The cyroablation component consisted of two cryoablation nozzles embedded in the cryoprobe. Both cryoablation nozzles were situated beneath the active RF electrodes near the junction between the RF electrodes to maximize the freezing between the RF electrodes. Each individually controlled cryoablation nozzle was capable of sustaining a maximum of 3500 psi supplied by an argon gas compressor manufactured by Galil Systems (Yokneam, Israel).

Example 2

Multi-applicator Arrays

The feasibility of multi-applicator RF/cryoablation arrays including two-, three-, and four-applicator arrays was assessed in ex-vivo liver (n=40) and in in-vivo liver (n=13). Based upon single-applicator results, current was applied at 0.6 amperes per applicator in the array. However, a generator limitation of 2.0 amperes prevented the application of 2.4 amperes for 4-applicator arrays and thus only 2.0 amperes was used. In ex-vivo liver, arrays were initially spaced at 0.5 cm and then increased at 0.5 cm intervals until maximum contiguous coagulation was achieved. Once an optimal spacing was achieved, multiple ablations were performed at that spacing for statistical analysis. Optimal arrays assessed included: (a) two-applicators (n=4) at 1.2 amp, 3000 psi, 2.5 cm spacing, 15 min, (b) three-applicators (n=3) at 1.8 amp, 3000 psi, 3.0 cm-triangular spacing, 15 min, and (c) four-applicators arrays (n=3) at 2.0 amp, 3000 psi, 3.0 cm-square spacing, 15 min.

For in-vivo liver, arrays of multiple applicators were assessed for a treatment duration of 20 minutes (n=13). Based upon smaller in-vivo coagulation diameters for a single applicator, the spacing between applicators in the arrays was decreased from optimal ex-vivo spacing by 0.5-1.0 cm to ensure contiguous coagulation. Thus, multi-applicator arrays assessed included: (a) two-applicators (n=3) at 1.2 amp, 3000 psi, 1.5 cm spacing, 20 min, (b) three-applicators (n=3) at 1.8 amp, 3000 psi, 2.0 cm-triangular spacing, 20 min, and (c) four-applicators arrays (n=3) at 2.0 amp, 3000 psi, 2.5 cm-square spacing, 20 min.

Example 3

Ex-Vivo Bovine Liver Ablation

Radiofrequency ablation alone was performed (n=18) in ex-vivo bovine liver obtained from a local butcher for 15 minutes for a range of current (0.3-0.6 amps) tested at 0.1 ampere intervals. For rises in impedance $40\Omega$ above baseline, pulsing was performed manually by discontinuing power until the impedance returned to baseline and then slowly increasing power back to the starting current. The current yielding the largest short-axis coagulation diameter was defined as the optima. Multiple trials were performed (n=10) under optimal parameters for comparison to cyroablation alone and combination RF/cryoablation.

Cryoablation alone was performed (n=10) by activating both cyroablation nozzles for 15 minutes at the maximum pressure allowed by the device (3500 psi). After 15 minutes of intense freezing, the tissue was thawed using helium gas for 4 minutes (confirmed with ultrasound), and the cycle repeated for a total of two freeze-thaw cycles. This method was deemed optimal based upon previous protocols using argon gas cryoablation. Changes in tissue impedance were measured by comparing values obtained prior to cryoablation and during the cryoablation treatment by moving one of the bipolar device electrodes into the frozen tissue.

Combination RF/cryoablation was performed (n=62) in ex-vivo bovine liver for 15 minutes for a matrix of current (0.4-0.7 amps) and argon pressure (1000-3500 psi). Pulsing was performed as described for impedance rises ($40\Omega$) above the baseline. Once optimal parameters were determined, multiple trials at 15 minutes were performed (n=8) under optimal parameters (0.6 amp, 3000 psi) to enable representative comparison of the combined method to RF ablation alone and cryoablation alone. Next, treatment duration was varied from 5 to 42 minutes (n=37) in a single combination RF/cryoablation applicator under optimal settings (0.6 amp, 3000 psi).

The optimal applied current for RF ablation alone for 15 minutes was 0.4 amperes for a single electrode, achieving a coagulation diameter of 1.5±0.3 cm in the short axis. Multiple impedance rises (7±3 per min) were observed during trials at 0.4 amperes but baseline impedance was adequately recovered with pulsing. The application of current above 0.4 amperes produced sharp rises in impedance 1-2 minutes into the trial that could not be reversed with pulsing, resulting in premature termination of treatment. Though fewer rises in impedance were observed with the application of 0.4 amperes, this resulted in smaller diameters of coagulation.

For cryoablation alone, the cross-section of the frozen tissue visualized by ultrasound during freeze cycles at maximum 3500 psi pressure measured 1.6±0.3 cm. Gross examination revealed an area of frozen tissue corresponding to the area observed sonographically but no permanent alteration in color or texture was observed. The application of cryoablation increased impedance from 156±10Ω before treatment to >1000Ω during treatment.

Combination RF/cryoablation enabled the application of more than 0.4 amp without rapid impedance rises, and in general, significantly fewer impedance rises were observed with optimal combination RF/cryoablation (2±1 per min) than with optimal RF ablation alone (7±3 per min, p<0.01). Combining cryoablation with RF also substantially increased the extent of coagulation when compared to optimal RF ablation alone or cyroablation alone. The greatest amount of coagulation for a single applicator was observed at a ratio of 3000 psi and 0.6 amp that achieved a short-axis coagulation diameter of 3.6±0.4 cm, significantly greater than RF ablation alone (1.5±0.3, p<0.01) or cryoablation alone (1.6±0.3 cm, p<0.01).

Figure 14A:
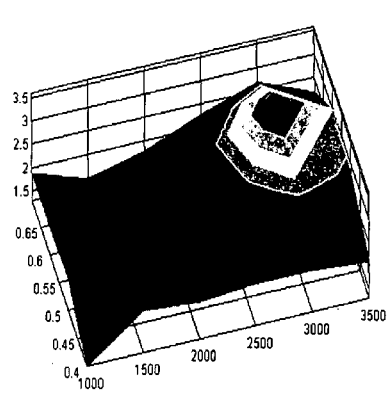
FIGS. 14A and 14B are contour plots illustrating the relationship between x-axis argon pressure (psi) and y-axis RF current (amperes) for a single RF/cryoablation applicator in ex-vivo bovine liver in FIG. 14A and in in-vivo bovine liver in FIG. 14B, with the short-axis diameter of coagulation (cm) represented in the z-axis by shaded contours.
Figure 14B:
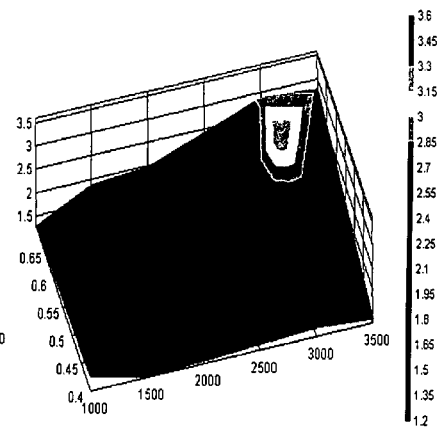

Multivariate regression analysis of radiofrequency current and argon freezing pressure revealed the extent of coagulation to be closely related to the combination of both parameters with an $R^2$ value of 0.68. Univariate regression analysis of coagulation against each parameter separately revealed an association with argon pressure ($R^2$=0.49) and radiofrequency current ($R^2$=0.20). Both parameters produced parabolic responses for tissue coagulation with an optimal ratio of pressure and current suggested by the peak of the two intersecting parabolic functions. FIGS. 14A-B show contour plots illustrating the relationship between x-axis argon pressure (psi) and y-axis RF current (amperes) for a single RF/cryoablation applicator in (A) ex-vivo and (B) in-vivo bovine liver. The short-axis diameter of coagulation (cm) is represented in the z-axis by shaded contours. Both graphs reveal optima at 3000 psi argon pressure and 0.6 amp RF current. The only notable difference between the maps is the decrease in amplitude (coagulation diameter) from ex-vivo to in-vivo liver ablations.

Figure 15:
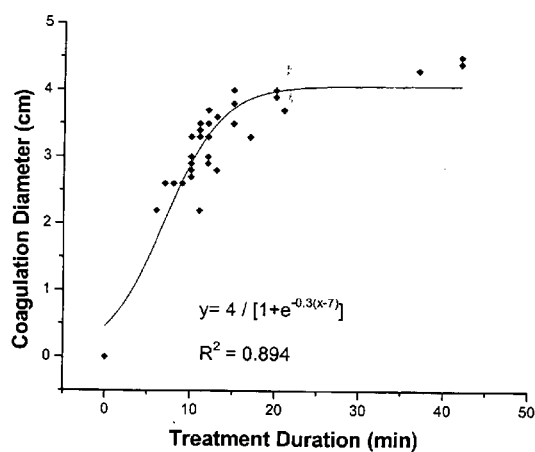
FIG. 15 is a plot of coagulation diameter (cm) versus treatment duration (min) for a single combination RF/cryoablation applicator in ex-vivo bovine liver.

As shown in FIG. 15, regression analysis of treatment duration approximated a sigmoidal function with an $R^2$ value of 0.89. The curve reveals 90% of coagulation to be achieved in the first 20 minutes of treatment with nominal increases in coagulation achieved for longer durations. A single applicator achieved 3.9±0.2 cm (n=3) after 20 minutes and 4.4±0.1 cm (n=3) if extended up to 42 minutes.

The greatest extent of contiguous coagulation in a 2-applicator array of combination RF/cryoablation after a 15-minute treatment (1.2 amp, 3000 psi) was achieved with the applicators spaced 2.5 cm apart, yielding a short-axis coagulation diameter of 5.3±0.1 cm. An array of 3-applicators in a triangular pattern (1.8 amp, 3000 psi, 15 min), optimally spaced at 3 cm apart, achieved 6.4±0.1 cm of confluent coagulation. A square array of four applicators at 3.5 cm spacing achieved 7.6±0.1 cm of confluent coagulation. Applicators spaced closer than the optimal spacing achieved smaller diameters of coagulation while further spacing did not always produce contiguous coagulation after a treatment duration of 15 minutes.

Table 1 shows a summary of short-axis coagulation diameters for ex-vivo bovine liver.

TABLE 1

| Configuration | Time (min) | Pulses/min | Coagulation diameter (cm) |
| --- | --- | --- | --- |
| Cryoablation alone | 15 (x2 cycles) | n/a | 1.6 cm ± 0.3 cm |
| RF ablation alone | 15 | 7 ± 3 | 1.5 cm ± 0.3 cm |
| RF/Cryo: single applicator | 15 | 2 ± 1 | 3.6 cm ± 0.4 cm |
| RF/Cryo: 2-applicator array (2.5 cm spacing) | 15 | 2 ± 1 | 5.3 cm ± 0.1 cm |
| RF/Cryo: 3-applicator array (3.0 cm spacing) | 15 | 1 ± 1 | 6.4 cm ± 0.1 cm |
| RF/Cryo: 4-applicator array (3.5 cm spacing) | 15 | 1 ± 1 | 7.6 cm ± 0.1 cm |

Pathologic studies also were performed on the ex-vivo liver. RF ablated tissue was excised and sectioned perpendicular to the applicator needle axis. The short-axis diameter of coagulation was assessed by gross examination with calipers. For cyroablation alone, the zone of frozen tissue was identified with ultrasonagraphy in real time as an area of hypoechocity with an echoic rim. The diameter of the frozen tissue representing the largest possible diameter of eventual necrosis was used for comparison. FIG. 16 shows a gross pathologic assessment of ex-vivo liver ablations with: (A) RF alone (0.4 amp), (B) RF/cryoablation single applicator (0.6 amp, 3000 psi), (C) RF/cryoablation 3-applicator (1.8 amp, 3000 psi) and (D) RF/cryoablation 4-applicator (2.0 amp, 3000 psi). The insertion points are labeled with reference numeral 160. The coagulations appear as lighter colored regions and are labeled with the reference numeral 162. All ablations were 15 minutes in duration.

Figure 16A:
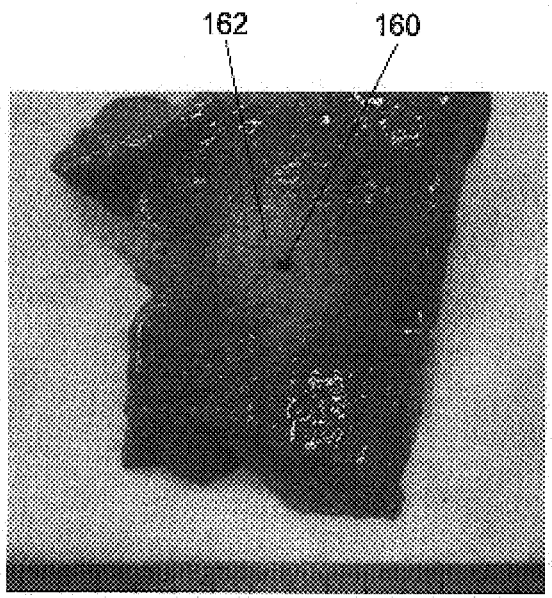
FIGS. 16A-16D are gross pathologic assessments of ex-vivo liver ablations for RF alone (0.4 amp) in FIG. 16A, RF/cryoablation single applicator (0.6 amp, 3000 psi) in FIG. 16B, RF/cryoablation 3-applicator (1.8 amp, 3000 psi) in FIG. 16C and RF/cryoablation 4-applicator (2.0 amp, 3000 psi) in FIG. 16D.
Figure 16B:
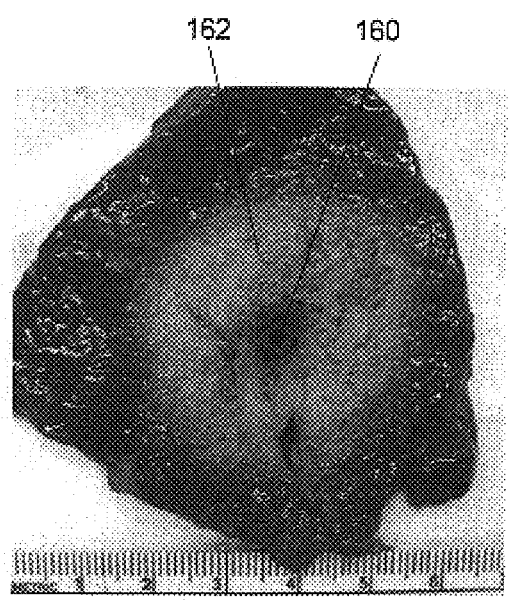
Figure 16C:
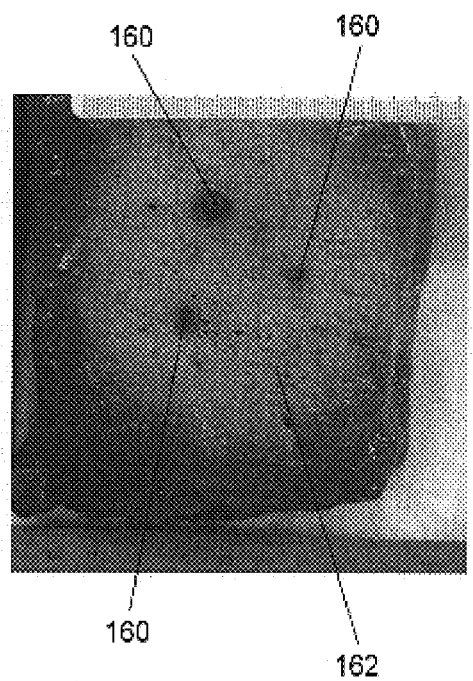
Figure 16D:
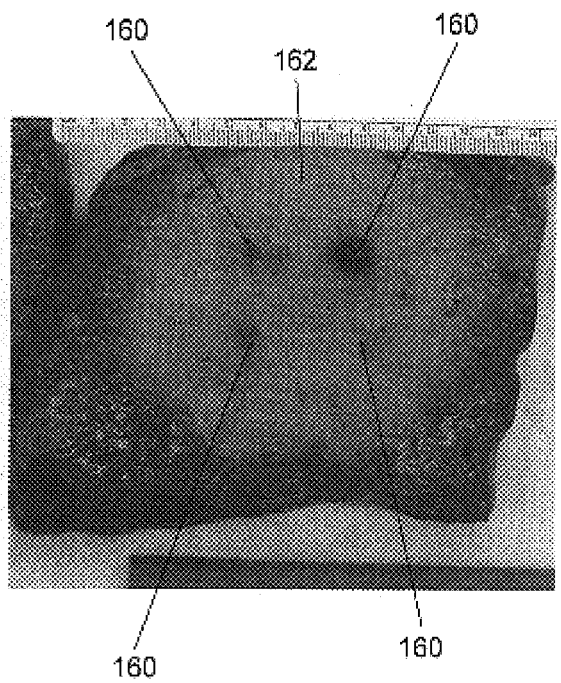

By visual comparison of FIG. 16A and FIG. 16B, it is clear that the combination of RF ablation and cryoablation resulted in a larger coagulation than cryoablation alone. FIGS. 16C and 16D show how the coagulation further increased in size when the applicator was staged in an array with other applicators.

Example 4

In-Vivo Porcine Liver Ablation

All animals were cared for according to the approved guidelines of the Institute of Animal Care and Use Committee (IACUC). Yorkshire pigs were obtained (Parkman Farms, Mass.) at a size of 70-80 kgs and were allowed to acclimate to the animal research facility for 48 hours before experimentation. Prior to the ablation procedure, the pigs were sedated via intramuscular administration of ketamine (15 mg/kg) and then intubated and maintained under a deep plane of anesthesia using isoflorane (1-4%). The abdomen was opened through a midline incision and an applicator was inserted into liver parenchyma under direct visualization. Ultrasound was used to position applicators away from as many vessels (>5 mm) as possible. Multiple applications were performed in each animal (maximum of three ablations per lobe). After all ablations were performed, the animal was euthanized with intravenous pentobarbital.

Radiofrequency ablation alone was performed (n=3) at the optimal duration of treatment (20 minutes) and device parameters (0.4 amperes) determined from ex-vivo studies. The same pulsing algorithm utilized for ex-vivo studies was employed for in-vivo studies to recover impedance rises (40Ω) above the baseline. Cryoablation alone (n=3) was performed in in-vivo porcine liver by activating both cyroablation nozzles for 20 minutes at 3500 psi. The tissue then was thawed using helium gas for 4 minutes (confirmed using ultrasound). The cycle was repeated for a total of two freeze-thaw cycles. Combination RF/cryoablation (n=49) was performed for 20 minutes for a matrix range of current (0.4-0.7 amp, 0.1 amp intervals) and argon pressure (1000-3500 psi, 500 psi intervals).

RF ablation alone (0.4 amp, 20 minutes) in in-vivo porcine liver achieved a cross-sectional diameter of 1.1±0.1 cm with a length of 4.5±0.5 cm. Multiple impedance rises (8±5 per min) also were observed beginning at minute 1-2 and lasting until the end of treatment. Attempts to apply current greater than 0.4 amp resulted in rapid irreversible impedance rises within the first minute of treatment, resulting in premature termination of RF application.

With cryoablation alone, the zone of destruction measured 1.3±0.1 cm by 2.9±0.1 cm while the frozen tissue diameter was slightly larger (1.5±0.2 cm). The application of cryoablation increased impedance from 87±4Ω before treatment to >1000Ω during treatment.

Substantial gains in coagulation were again observed for combination RF/cryoablation when compared to RF ablation alone or cryoablation alone. After 20 minutes, a single RF/cryoablation applicator at optimal settings (0.6 amp, 3000 psi) yielded 3.2±0.3 cm by 6.3±0.1 cm of contiguous coagulation, significantly greater in both axes than optimal RF ablation alone (1.1±0.1 cm by 4.5±0.5 cm, p<0.01) and cryoablation alone (1.3±0.1 cm by 2.9±0.1 cm, p<0.01). Significantly fewer impedance rises were observed during RF/cryoablation (2±1 per min) than were observed during RF ablation alone (7±3 per min, p<0.01).

When comparing coagulation between in-vivo and ex-vivo, the in-vivo short-axis diameter for RF/cryoablation was slightly smaller (3.2±0.3 cm) than ex-vivo (3.6±0.3 cm, p=0.3) despite an additional 5 minutes of treatment for in-vivo ablation. Decreases in the short-axis diameter for in-vivo studies also were observed for RF ablation alone (ex-vivo: 1.5±0.3 cm, in-vivo: 1.1±0.1 cm) and cryoablation alone (frozen tissue ex-vivo: 1.6±0.3 cm, frozen tissue in-vivo: 1.5±0.1 cm).

Multivariate regression analysis of radiofrequency current and argon freezing pressure revealed an optimal ratio of 3000 psi pressure and 0.6 amp current which was identical to the optimal ratio of pressure and current for ex-vivo studies. The shape of the surface contour map also was very similar to ex-vivo with regression studies revealing the combination of both parameters to be associated with coagulation diameter. The $R^2$ for multivariate regression of both parameters was 0.63, similar to the association for ex-vivo liver (0.68). As seen in FIG. 14, both parameters again showed greatest correlation to a parabolic function with an optimal peak ratio of pressure and current. Univariate regression against each parameter revealed an association with argon pressure ($R^2$=0.52) and current ($R^2$=0.36). Overall, the R-squares were stronger for argon pressure (ex-vivo: 0.49, in-vivo: 52) than current (ex-vivo: 0.20, in-vivo: 0.36).

After 20 minutes of treatment, two-applicator arrays (1.2 amp, 3000 psi, 2.0 cm spacing) yielded a confluent zone of coagulation measuring 5.1±0.2 cm by 6.5±1.3 cm, and triangular three-applicator arrays (1.8 amp, 3000 psi, 2.5 cm spacing) yielded 5.8±0.5 cm by 7.3±0.7 cm. Square arrangements of 4-applicator arrays (2.0 amp, 3000 psi, 2.5 cm spacing) yielded a confluent zone of coagulation measuring 7.0±0.5 cm by 8.0±0.5 cm. Applicators spaced further apart than the optimal spacing yielded disconnected areas of coagulation while applicators spaced closer than the optimal setting yielded smaller diameters of coagulation. In some multi-applicator ablations, vessels as large as 7 mm were observed within the area of contiguous coagulation.

Figure 17:
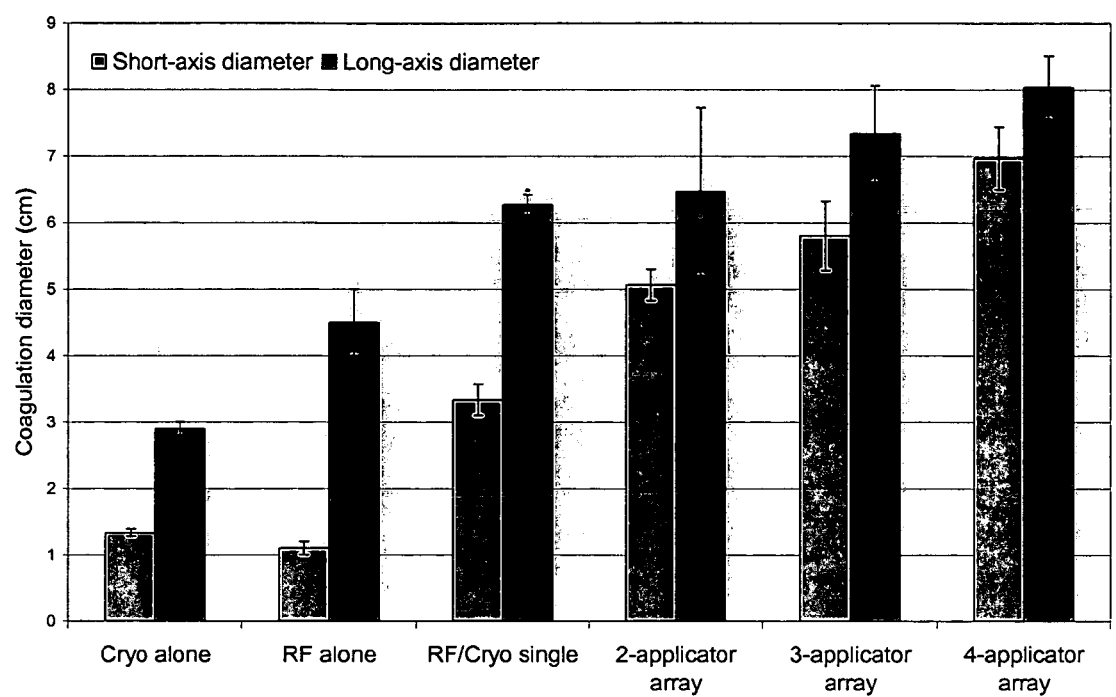
FIG. 17 shows the in-vivo coagulation diameters along short-axis (perpendicular to applicator) and long-axis (applicator axis) after 20 minutes duration for various applicators and applicator combinations.

FIG. 17 shows the in-vivo coagulation diameters along short-axis (perpendicular to applicator) and long-axis (applicator axis) after 20 minutes duration for various applicators and applicator combinations. Significant gains in coagulation were achieved in both the short-axis and long-axis with combination RF/cryoablation compared to cryoablation alone and RF ablation alone. Further gains in coagulation were achieved with multi-applicator arrays.

Immediately after animal euthanization, the liver was removed en bloc and ablated tissue was sectioned along the long axis. Cell viability, measured by mitochondrial enzyme activity, was assessed by incubating tissue sections for 30 minutes in 2% 2,3,5-triphenyl tetrazolium chloride (TTC) at 20° C.-25° C. The absence of mitochondrial enzyme activity has been shown to accurately reveal irreversible cellular injury induced by percutaneous tumor ablation. With this method, viable tissue with intact mitochondrial enzyme activity is stained red while ablated tissue does not reveal a red color. Calipers were used to measure the extent of gross coagulation in the short-axis (perpendicular to needle) and long-axis (along needle axis) of the ablation. Additionally, completeness of ablation was assessed in binary fashion either as to whether the zone of coagulation necrosis was or was not completely contiguous. FIG. 18 is a gross pathologic assessment of in-vivo porcine liver ablations using RF/cryoablation with: (A) 1-applicator (0.6 amp, 3000 psi), (B) 2-applicators (1.2 amp, 3000 psi, 1.5 cm spacing), (C) 3-applicators (1.8 amp, 3000 psi, 2.0 cm spacing) and (D) 4-applicators (2.0 amp, 3000 psi, 2.5 cm spacing). Vessels up to 7 mm in diameter were noted within most multi-applicator ablations, such as vessels 164 in FIGS. 18C and 18D.

Figure 18A:
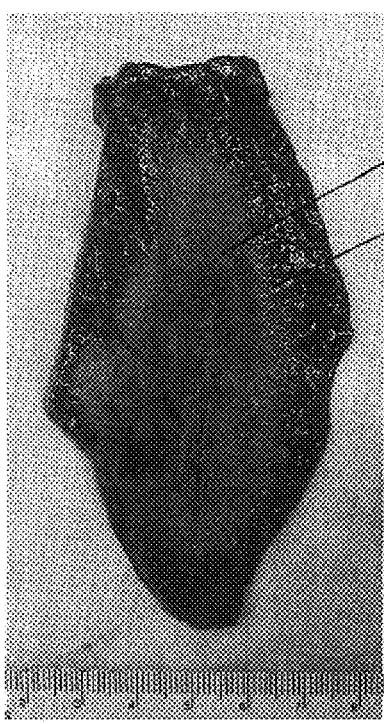
FIGS. 18A-18D are gross pathologic assessments of in-vivo porcine liver ablations using RF/cryoablation with: 1-applicator (0.6 amp, 3000 psi) in FIG. 18A, 2-applicators (1.2 amp, 3000 psi, 1.5 cm spacing) in FIG. 18B, 3-applicators (1.8 amp, 3000 psi, 2.0 cm spacing) in FIG. 18C and 4-applicators (2.0 amp, 3000 psi, 2.5 cm spacing) in FIG. 18D.
Figure 18B:
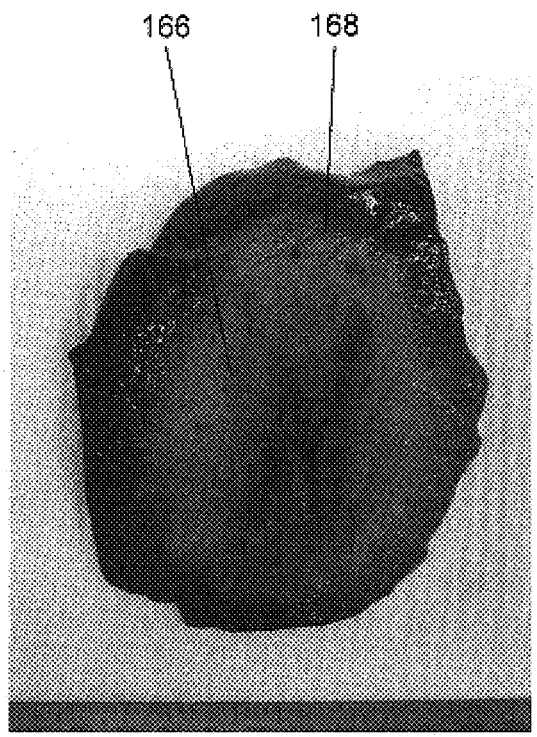
Figure 18C:
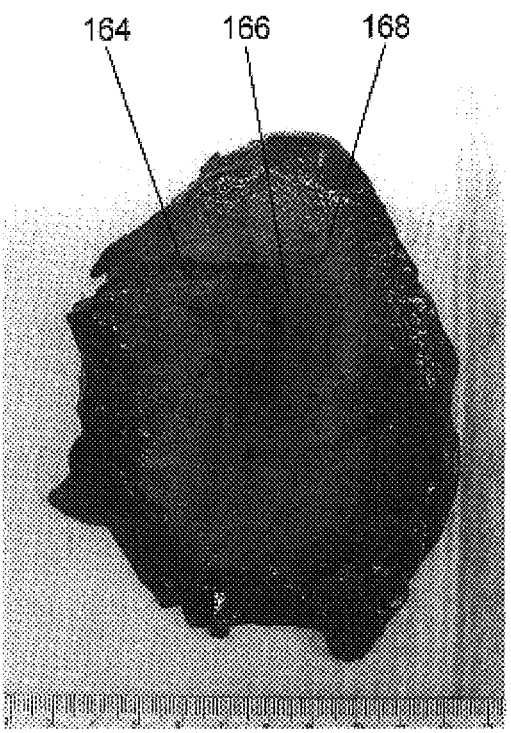
Figure 18D:
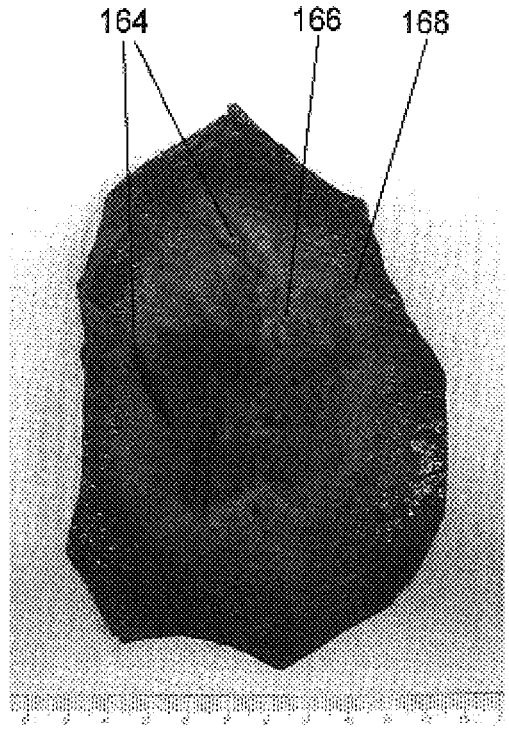

The coagulations in FIGS. 18A-18C are labeled with the reference numeral 166. The exact boundary of the tissue necrosis can only be determined by pathological assessment of the tissue under magnification, but a clear distinction can be seen between tissue stained dark red and tissue with significantly less coloration at a border 168 of each coagulation 166. As discussed above, the dark red stain indicates cell viability, so the transition between dark red and lighter red at the border 168 is a good estimate of the boundary of the coagulation. Based on the coloration of the samples shown in FIGS. 18A-18D, it is evident that each additional applicator used in the ablation procedure increased the size of the resulting coagulation.

CLOSING

While preferred embodiments and methods have been described herein, it should be apparent to those skilled in the art that variations and modification are possible without departing from the spirit of the invention as set out in the following claims.

I claim:

1. A cryosurgical apparatus, comprising:
    a cryoprobe having an elongated length, a proximal end, a distal end, an electrically conductive first portion and first and second independently controllable cooling elements;
    an energy conducting element coupled to the cryoprobe and having an electrically conductive second portion in a region spaced apart from the first portion; and
    electrical insulation interposed between the first portion and the second portion,
    wherein the cryosurgical apparatus is configured to be at least partially inserted into tissue and, upon activation, to cool the tissue in a cooling region adjacent to the cryoprobe by selectively controlling the first and second cooling elements and to produce heating of the tissue around the cooling region by controlling the flow of energy through the tissue being heated, wherein the energy is transmitted between the first portion and the energy conducting element, and wherein the cooling region is located substantially between the first portion and the energy conducting element.

2. The cryosurgical apparatus of claim 1, wherein the first cooling element comprises a first Joule-Thomson nozzle and the second cooling element comprises a second Joule-Thomson nozzle, and the first and second Joule-Thomson nozzles are spaced apart along the length of the cryoprobe between the proximal end and the distal end.

3. The cryosurgical apparatus of claim 1, further comprising a first variable supply valve for controlling the flow of cryogenic medium into the first cooling element and a second variable supply valve for controlling the flow of cryogenic medium into the second cooling element.

4. The cryosurgical apparatus of claim 1, wherein the energy conducting element surrounds a portion of the cryoprobe, and the electrical insulation is disposed between the cryoprobe and the energy conducting element.

5. The cryosurgical apparatus of claim 1, wherein the energy conducting element comprises an elongate electrically and thermally conductive sheath coaxially surrounding a portion of the cryoprobe with a distal end of the energy conducting element exposed and a layer of electrically insulating material covering remaining portions of the electrically conducting element.

6. The cryosurgical apparatus of claim 1, wherein the first cooling element comprises a first heat exchanger comprising a first serpentine tube portion, a first supply tube and a first nozzle, and the second cooling element comprises a second heat exchanger comprising a second serpentine tube portion, a second supply tube and a second nozzle.

7. The cryosurgical apparatus of claim 6, wherein the first nozzle is positioned between the first serpentine tube portion and the second serpentine tube portion.

8. The cryosurgical apparatus of claim 6, wherein the second serpentine tube portion is positioned between the first serpentine tube portion and the distal end of the cryoprobe.

9. The cryosurgical apparatus of claim 8, wherein the first serpentine tube portion is wrapped around the second supply tube.

10. The cryosurgical apparatus of claim 1, further comprising an electromagnetic energy generator, wherein the first portion is operatively connected to the electromagnetic energy generator and the second portion is operatively connected to electrical ground or the second portion is operatively connected to the electromagnetic energy generator and the first portion is operatively connected to electrical ground.

11. The cryosurgical apparatus of claim 10, wherein the electromagnetic energy generator is a variable frequency energy generator.

12. The cryosurgical apparatus of claim 10, wherein the electromagnetic energy generator is a radiofrequency energy generator.

13. A method for performing tissue ablation, comprising: inserting a cryosurgical apparatus with an elongated length into tissue in a treatment area;
killing tissue in a first zone adjacent to the cryosurgical apparatus by freezing the tissue in the first zone; and
killing tissue in a second zone surrounding the first zone by heating the tissue in the second zone with electromagnetic energy, the second zone having at least a portion that is isolated from the apparatus by the surrounded first zone.

14. The method of claim 13, wherein the first zone and the second zone together define an ablation zone, the ablation zone has an ablation axis extending perpendicular to the length of the cryosurgical apparatus, and further comprising killing tissue in the first zone and the second zone until the ablation zone has a dimension along the ablation axis greater than about 3 centimeters.

15. A method for performing tissue ablation, comprising:
inserting a cryosurgical apparatus into tissue in a treatment area;
killing tissue in a first zone adjacent to the cryosurgical apparatus by heating the tissue in the first zone with electromagnetic energy;
cooling the tissue in the first zone to create a tissue electrical conductivity differential between the tissue in the first zone and tissue in a second zone adjacent and outward from the first zone, the second zone having at least a portion that is isolated from the apparatus by the first zone, wherein the tissue in the second zone has a higher electrical conductivity than the tissue in the first zone; and
killing tissue in the second zone by heating the tissue in the second zone with electromagnetic energy.

16. A method for performing tissue ablation, comprising:
inserting an ablation apparatus with an elongated length into tissue to be treated, the ablation apparatus having a first electrode and a second electrode;
cooling the tissue in a cooling region adjacent to a first area and a second area on the ablation apparatus by cooling the ablation apparatus at the first area and the second area, wherein the first area and the second area are spaced apart along the length of the ablation apparatus; and
conveying electromagnetic energy through the tissue outside of the cooling region between the first electrode and the second electrode, wherein the act of cooling allows a greater amount of tissue to be ablated with a given quantity of electromagnetic energy.

17. The method of claim 16, wherein the first electrode is separated from the second electrode along the length of the ablation apparatus by an insulating distance, and further comprising modifying a path taken by the electromagnetic energy by changing the insulating distance.

18. The method of claim 16, wherein the ablation apparatus has at least a first heat exchanger and a second heat exchanger, and further comprising modifying the cooling activity of the ablation apparatus at the first area or the second area by adjusting the flow of a cooling medium to the first heat exchanger or the second heat exchanger, respectively.

19. The method of claim 16, further comprising forming a coagulation in the tissue, wherein the coagulation has a shape comprising a first ellipsoid positioned around the first area and a second ellipsoid positioned around the second area.

* * * * *